(12) United States Patent
Wang et al.

(10) Patent No.: US 11,923,071 B2
(45) Date of Patent: *Mar. 5, 2024

(54) MULTI-PHASE OBJECT CONTOUR REFINEMENT

(71) Applicant: INTERNATIONAL BUSINESS MACHINES CORPORATION, Armonk, NY (US)

(72) Inventors: Yi-Qing Wang, Paris (FR); Moshe Raboh, Holon (IL); Dana Levanony, Tel Aviv (IL); Giovanni John Jacques Palma, Chaville (FR)

(73) Assignee: International Business Machines Corporation, Armonk, NY (US)

( * ) Notice: Subject to any disclaimer, the term of this patent is extended or adjusted under 35 U.S.C. 154(b) by 499 days.

This patent is subject to a terminal disclaimer.

(21) Appl. No.: 17/191,166

(22) Filed: Mar. 3, 2021

(65) Prior Publication Data

US 2022/0285008 A1    Sep. 8, 2022

(51) Int. Cl.
*G06K 9/00*      (2022.01)
*G06N 3/08*      (2023.01)
(Continued)

(52) U.S. Cl.
CPC .............. *G16H 30/40* (2018.01); *G06N 3/08* (2013.01); *G06T 7/0012* (2013.01); *G06T 7/11* (2017.01);
(Continued)

(58) Field of Classification Search
CPC . G16H 30/40; G06N 3/08; G06N 3/02; G06T 7/0012; G06T 7/11;
(Continued)

(56) References Cited

U.S. PATENT DOCUMENTS 6,430,430 B1 *   8/2002   Gosche ................... G06T 7/155
                                                        128/923
10,881,358 B2 *  1/2021   Fredenberg ............ A61B 6/482
                      (Continued)

FOREIGN PATENT DOCUMENTS

WO        2020/190821 A1    9/2020

OTHER PUBLICATIONS

Wang et al., "Multi-phase object contour refinement", U.S. Appl. No. 17/191,158, filed Mar. 3, 2021, 32 pages.
(Continued)

*Primary Examiner* — Shervin K Nakhjavan
(74) *Attorney, Agent, or Firm* — Jordan T. Schiller

(57) ABSTRACT

A method and system perform single phase and multi-phase contour refinement of lesions. The method includes receiving a three dimensional input mask; receiving input slices from the medical images including a lesion; cropping the input slices with the input mask; performing lesion contour refinement for the cropped input slices and the input mask to obtain a predicted mask; and storing the predicted mask that includes 3D lesion contour refinement. A multiphase method includes deforming the 3D input mask from the reference phase to a target phase or warping the input slices from the target phase to the reference phase before contour refinement. The warped images generate an output mask in the reference phase coordinate system that is then deformed to the target phase coordinate system for display.

17 Claims, 12 Drawing Sheets

(51) Int. Cl.
 *G06T 7/00* (2017.01)
 *G06T 7/11* (2017.01)
 *G16H 30/40* (2018.01)
(52) U.S. Cl.
 CPC ............... *G06T 2207/10081* (2013.01); *G06T 2207/20081* (2013.01); *G06T 2207/20084* (2013.01); *G06T 2207/30096* (2013.01); *G06T 2210/22* (2013.01)
(58) Field of Classification Search
 CPC . G06T 2207/10081; G06T 2207/20081; G06T 2207/20084; G06T 2207/30096; G06T 2210/22; G06T 7/149; G06T 7/12
 See application file for complete search history.

(56) References Cited

U.S. PATENT DOCUMENTS

| | | | | |
|---|---|---|---|---|
| 11,227,683 | B2* | 1/2022 | Morard | G06T 7/0014 |
| 2004/0087850 | A1* | 5/2004 | Okerlund | G16H 30/40 600/407 |
| 2009/0022375 | A1* | 1/2009 | Fidrich | G06T 5/50 382/128 |
| 2009/0097726 | A1* | 4/2009 | Rusko | G06T 7/187 382/131 |
| 2009/0129673 | A1* | 5/2009 | Simon | G06T 7/0012 382/128 |
| 2010/0215238 | A1* | 8/2010 | Lu | G06T 7/12 382/131 |
| 2011/0158491 | A1* | 6/2011 | Markova | G06T 3/0081 382/128 |
| 2015/0078640 | A1 | 3/2015 | Guo et al. | |
| 2015/0302601 | A1 | 10/2015 | Rivet-Sabourin | |
| 2019/0066303 | A1 | 2/2019 | Neelapu | |
| 2019/0128986 | A1* | 5/2019 | Helle | G01R 33/56366 |
| 2019/0163950 | A1 | 5/2019 | Zhang | |
| 2019/0164291 | A1* | 5/2019 | Wang | G06V 10/50 |
| 2020/0085382 | A1* | 3/2020 | Taerum | G06T 7/0016 |
| 2020/0121951 | A1* | 4/2020 | Morgas | A61N 5/1067 |
| 2020/0138521 | A1* | 5/2020 | Aben | G06T 17/00 |
| 2020/0334825 | A1 | 10/2020 | Gooding | |
| 2021/0035290 | A1* | 2/2021 | Aben | A61B 5/0044 |
| 2021/0077077 | A1* | 3/2021 | Mitra | A61B 8/5261 |
| 2021/0224603 | A1* | 7/2021 | Yan | G06V 10/255 |
| 2021/0401392 | A1* | 12/2021 | Bengtsson | A61B 6/5217 |
| 2022/0180524 | A1 | 6/2022 | Novosad | |
| 2022/0284569 | A1* | 9/2022 | Wang | G06T 7/12 |
| 2022/0284588 | A1* | 9/2022 | Wang | G06T 7/149 |

OTHER PUBLICATIONS

Wang et al., "Multi-phase object contour refinement", U.S. Appl. No. 17/191,180, filed Mar. 3, 2021, 32 pages.
List of IBM Patents or Patent Applications Treated as Related, Jun. 7, 2021, 2 pages.
Estrada et al., "Multi-Scale Contour Extraction Based on Natural Image Statistics," Proceedings of the 2006 Conference on Computer Vision and Pattern Recognition Workshop (CVPRW'06), Published Date: Jul. 5, 2006, 8 pages.
Guo et al., "Fast and Refined Cancer Regions Segmentation Framework in Whole-slide Breast Pathological Images," Scientific Reports, May 20, 2019, 9:882, 10 pages.
ip.com, "Visualization Of Multi-Phase Contrast-Enhanced CT Images," <https://priorart.ip.com/IPCOM/000250898> Published Date: Sep. 13, 2017, 5 pages.
Wang et al., "Contour detection refined by a sparse reconstruction-based discrimination method," SIViP, 12:207-214, Published Online: Jul. 21, 2017.
Yang et al., "Object Contour Detection with a Fully Convolutional Encoder-Decoder Network," arXiv: 1603.04530v1, Published Date: Mar. 15, 2016, 10 pages.
Hoogi et al., "Adaptive Estimation of Active Contour Parameters Using Convolutional Neural Networks and Texture Analysis", IEEE Transactions on Medical Imaging, vol. 36, No. 3, pp. 781-791, Mar. 2017.
Hong, "A preliminary study on artificial neural network," 2011 6th IEEE Joint International Information Technology and Artificial Intelligence Conference, Chongqing, China, 2011, pp. 336-338.
Krizhevsky et al., "ImageNet classification with deep convolutional neural networks", Communications of the ACM, vol. 60, No. 6, Jun. 2017, pp. 84-90.
Wang et al., "Rigid Shape Matching by Segmentation Averaging," in IEEE Transactions on Pattern Analysis and Machine Intelligence, vol. 32, No. 4, pp. 619-635, Apr. 2010.

* cited by examiner

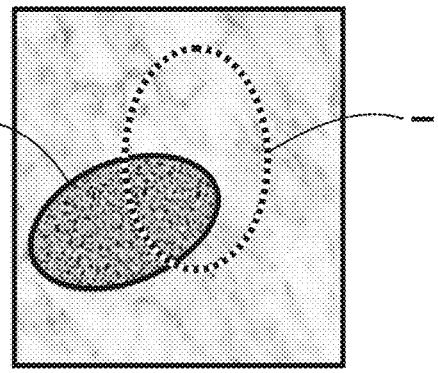
FIG. 4C
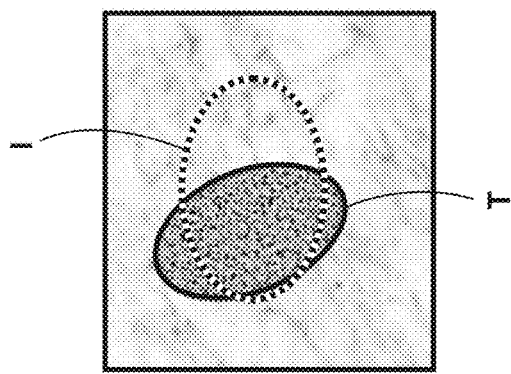
FIG. 4B
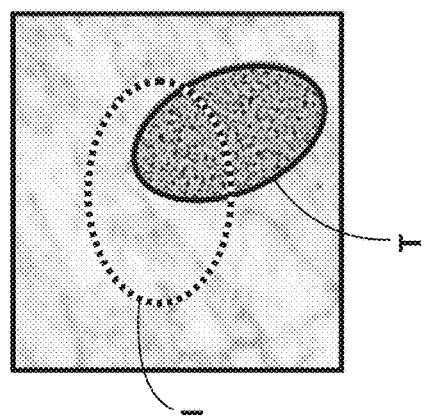
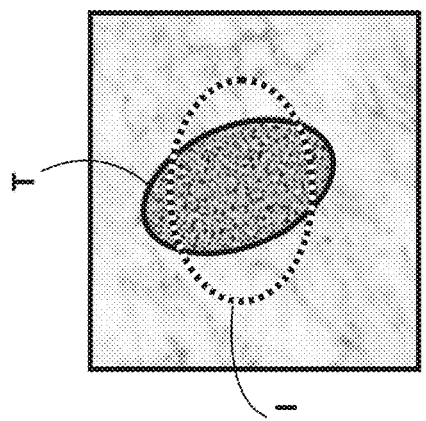
FIG. 4A
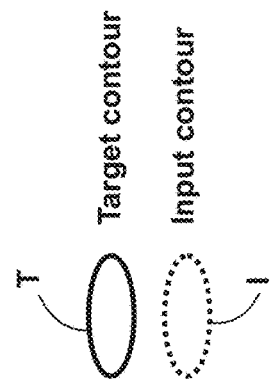

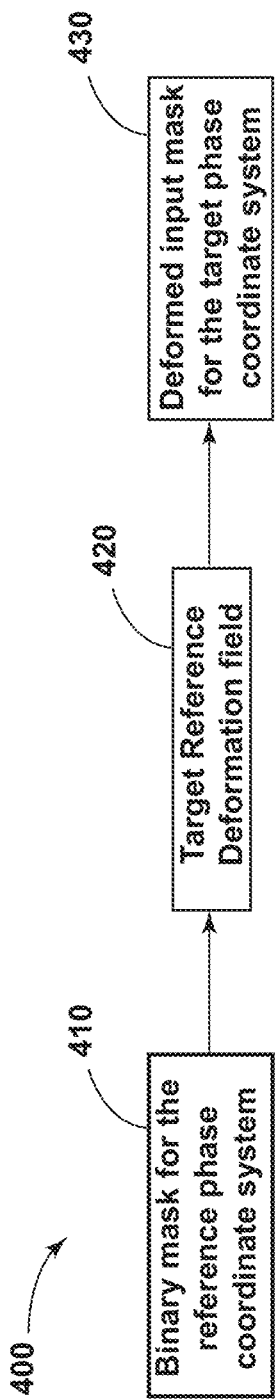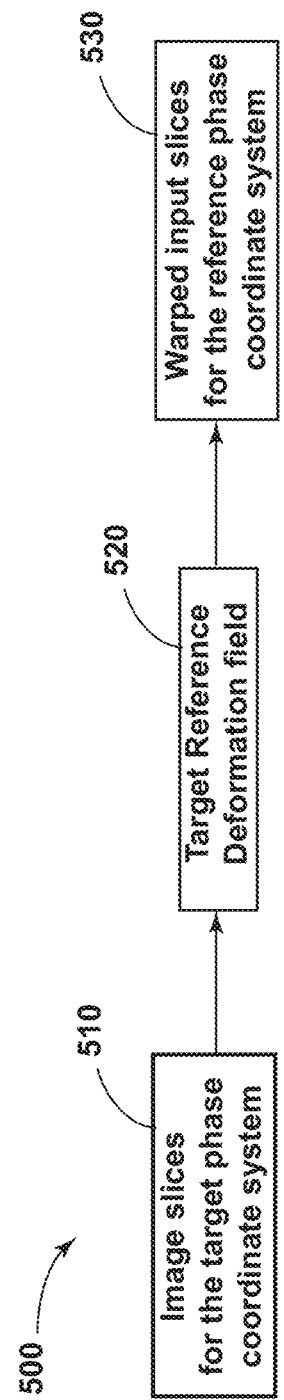
FIG. 8
FIG. 9

MULTI-PHASE OBJECT CONTOUR REFINEMENT

FIELD

Embodiments described herein relate to systems and methods for performing image analytics to refine the contour of objects in medical images.

SUMMARY

Semantic segmentation and instance segmentation are difficult tasks that may not share the same optimal operating point. Optimizing a semantic segmentation algorithm to determine most of the findings may lead to over/under segmentation of detected lesions if taken as is. Additionally, multi-image imaging (e.g. multiphase computerized tomography (CT) scans) bring another problem, which is instance identification across phase. This can be solved by expressing the detected finding of a lesion in a single/common coordinate system in order to identify instances and then refine segmentation of each identified lesion in the original phases.

One embodiment provides a system for providing lesion contour refinement for multiphase medical images of an organ. The system includes a display device, at least one memory for storing medical images, and an electronic processor. The electronic processor is configured to: receive a 3D input mask corresponding to a lesion contour determined for a reference phase of the multiphase medical images; deform the 3D input mask to correspond to point positions for a target phase coordinate system of the medical image to obtain a deformed input mask corresponding to a target phase; receive input slices from the target phase medical images that includes a lesion; crop the input slices to remove a sub-portion of the input slices; perform lesion contour refinement for the cropped input slices and the 3D input mask to obtain a 3D predicted mask; and store the 3D predicted mask for the target phase to provide a 3D lesion contour.

Another embodiment provides a method for providing lesion contour refinement for multiphase medical images of an organ. The method includes: receiving a 3D input mask corresponding to a lesion contour determined for a reference phase of the multiphase medical images; deforming the 3D input mask to correspond to point positions for a target phase coordinate system of the medical image to obtain a deformed input mask corresponding to a target phase; providing the deformed 3D input mask to a neural network; receiving input slices from the target phase medical images that includes a lesion; cropping the input slices to remove a sub-portion of the input slices; performing lesion contour refinement for the cropped input slices and the 3D input mask to obtain a 3D predicted mask; and storing the 3D predicted mask for the target phase to provide a 3D lesion contour.

A further embodiment provides a non-transitory computer medium including instructions that, when executed as a set of instructions by an electronic processor perform a set of operations. The set of operations include: receiving a 3D input mask corresponding to a lesion contour determined for a reference phase of the multiphase medical images; deforming the 3D input mask to correspond to point positions for a target phase coordinate system of the medical image to obtain a deformed input mask corresponding to a target phase; receiving input slices from the target phase medical images that includes a lesion; cropping the input slices to remove a sub-portion of the input slices; performing lesion contour refinement for the cropped input slices and the 3D input mask to obtain a 3D predicted mask; and storing the 3D predicted mask for the target phase to provide a 3D lesion contour.

Other aspects of the invention will become apparent by consideration of the detailed description and accompanying drawings.

BRIEF DESCRIPTION OF THE DRAWINGS

FIG. 4A shows an un-augmented training arrangement.

FIGS. 4B and 4C show different augmentation arrangements.

FIG. 8 shows a flowchart for deforming a binary three dimensional mask from a reference phase coordinate system to a target phase coordinate system.

FIG. 9 shows a flowchart for deforming image slices from a target phase coordinate system to warped image slices corresponding to a reference phase coordinate system.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

A plurality of hardware and software based devices, as well as a plurality of different structural components may be utilized to implement the invention. In addition, embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects of the invention may be implemented in software (e.g., stored on non-transitory computer-readable medium) executable by one or more processors. As such, it should be noted that a plurality of hardware and software based devices, as well as a plurality of different structural components, may be utilized to implement the invention. For example, "mobile device," "computing device," and "server" as described in the specification may include one or more electronic processors, one or more memory modules including non-transitory computer-readable medium, one or more input/output interfaces, and various connections (e.g., a system bus) connecting the components.

Figure 1:
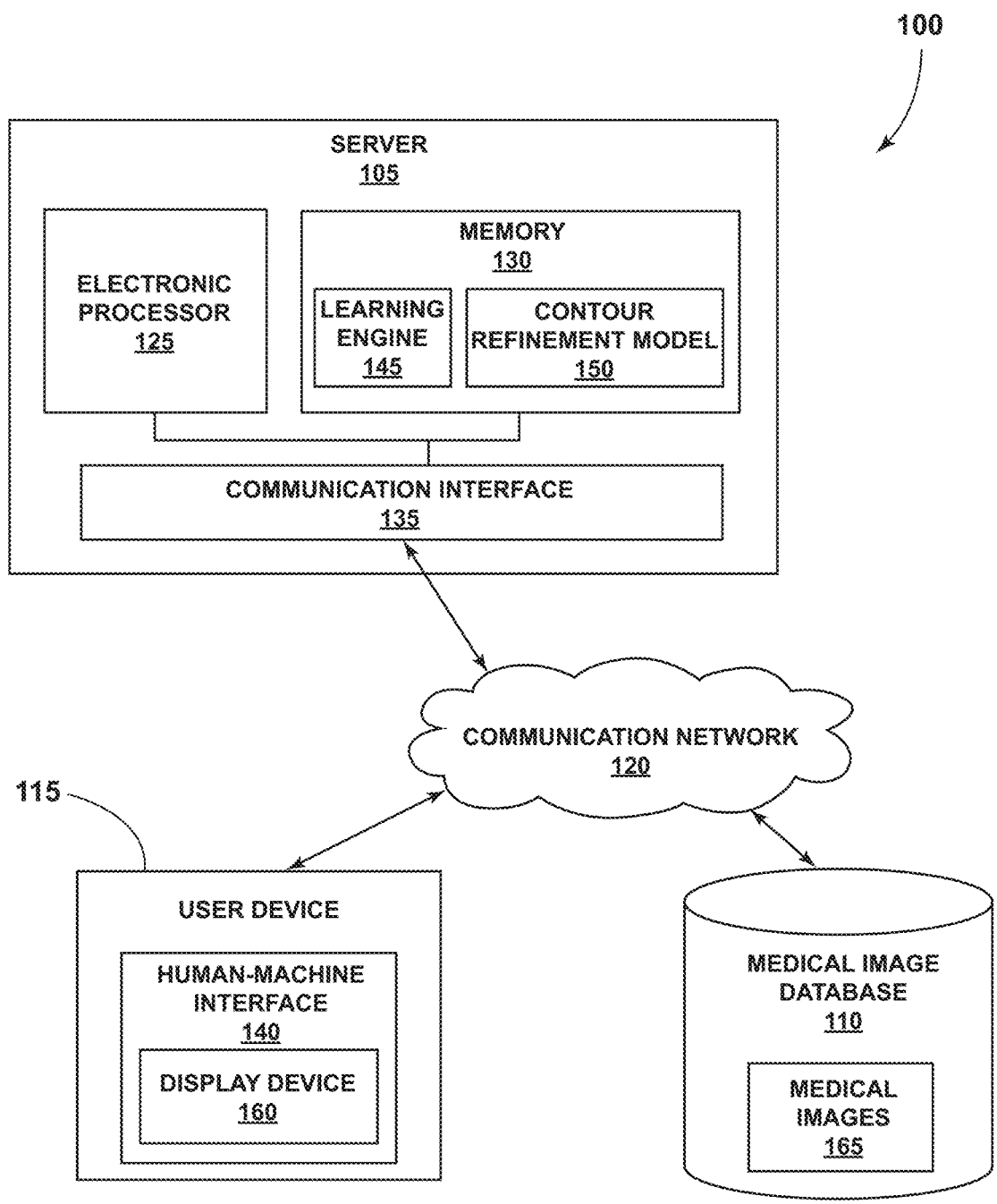
FIG. 1 illustrates a block diagram of a system for operating an artificial intelligence engine (AI) according to some embodiments for contour refinement.

FIG. 1 illustrates a system 100 for an AI engine according to some embodiments. The system 100 includes a server 105, a medical image database 110, and a user device 115. In some embodiments, the system 100 includes fewer, additional, or different components than illustrated in FIG. 1. For example, the system 100 may include multiple servers 105, medical image databases 110, user devices 115, or a combination thereof.

The server 105, the medical image database 110, and the user device 115 communicate over one or more wired or wireless communication networks 120. Portions of the communication network 120 may be implemented using a wide area network, such as the Internet, a local area network, such as a Bluetooth™ network or Wi-Fi, and combinations or derivatives thereof. Alternatively or in addition, in some embodiments, components of the system 100 communicate directly as compared to through the communication network 120. Also, in some embodiments, the components of the system 100 communicate through one or more intermediary devices not illustrated in FIG. 1.

The server 105 is a computing device, which may serve as a gateway for the medical image database 110. For example, in some embodiments, the server 105 may be a commercial picture archive and communication system (PACS) server. Alternatively, in some embodiments, the server 105 may be a server that communicates with a PACS server to access the medical image database 110.

As illustrated in FIG. 1, the server 105 includes an electronic processor 125, a memory 130, and a communication interface 135. The electronic processor 125, the memory 130, and the communication interface 135 communicate wirelessly, over one or more communication lines or buses, or a combination thereof. The server 105 may include additional components than those illustrated in FIG. 1 in various configurations. The server 105 may also perform additional functionality other than the functionality described herein. Also, the functionality described herein as being performed by the server 105 may be distributed among multiple devices, such as multiple servers included in a cloud service environment. In addition, in some embodiments, the user device 115 may be configured to perform all or a portion of the functionality described herein as being performed by the server 105.

The electronic processor 125 includes a microprocessor, an application-specific integrated circuit (ASIC), or another suitable electronic device for processing data. The memory 130 includes a non-transitory computer-readable medium, such as read-only memory (ROM), random access memory (RAM) (for example, dynamic RAM (DRAM), synchronous DRAM (SDRAM), and the like), electrically erasable programmable read-only memory (EEPROM), flash memory, a hard disk, a secure digital (SD) card, another suitable memory device, or a combination thereof. The electronic processor 125 is configured to access and execute a set of computer-readable instructions ("software") stored in the memory 130. The software may include firmware, one or more applications, program data, filters, rules, one or more program modules, and other executable instructions. For example, the software may include a set of instructions and associated data for performing a set of functions, including the methods described herein. The software may function as a neural network in some embodiments.

For example, as illustrated in FIG. 1, the memory 130 may store a learning engine 145 and a contour refinement model 150. It should be understood that in some embodiments, the contour refinement model 150 may be located external to the server 105. In this embodiment, the server 105 may communicate with and access data from the contour refinement model 150 directly or through one or more of the communication network(s) 120. Also, in some embodiments, the contour refinement model 150 may be included in or part of the medical image database 110, the user device 115, or a combination thereof, which the server 105 may similarly access.

The communication interface 135 allows the server 105 to communicate with devices external to the server 105. For example, as illustrated in FIG. 1, the server 105 may communicate with the medical image database 110 through the communication interface 135. In particular, the communication interface 135 may include a port for receiving a wired connection to an external device (for example, a universal serial bus (USB) cable and the like), a transceiver for establishing a wireless connection to an external device (for example, over one or more communication networks 120, such as the Internet, local area network (LAN), a wide area network (WAN), and the like), or a combination thereof.

The server 102 may also communicate with user device 115 via the communication network 120. Broadly, a user, such as a clinician, uses user device 115 to interact with one or more of the learning engine 145, the contour refinement model 150, and the medical image database 110. Although not illustrated, the user device 115 may include similar components as the server 105 (an electronic processor, a memory, and a communication interface). As noted above, in some embodiments, a memory of the user device 115 may store the classification model database 150. Alternatively or in addition, the user device 115 may access the classification model database 150 (or a portion thereof) stored in the memory 130 of the server 105 (or another device external to the user device 115) via the communication network 120.

The user device 115 may also include a human-machine interface 140. The human-machine interface 140 may include one or more input devices, one or more output devices, or a combination thereof. Accordingly, in some embodiments, the human-machine interface 140 allows a user to interact with (for example, provide input to and receive output from) the user device 115. For example, the human-machine interface 140 may include a keyboard, a cursor-control device (for example, a mouse), a touch screen, a scroll ball, a mechanical button, a display device (for example, a liquid crystal display (LCD)), a printer, a speaker, a microphone, or a combination thereof. As illustrated in FIG. 1, in some embodiments, the human-machine interface 140 includes a display device 160. The display device 160 may be included in the same housing as the user device 115 or may communicate with the user device 115 over one or more wired or wireless connections. For example, in some embodiments, the display device 160 is a touchscreen included in a laptop computer or a tablet computer. In other embodiments, the display device 160 is a monitor, a television, or a projector coupled to a terminal, desktop computer, or the like via one or more cables.

The medical image database 110 stores a plurality of medical images 165. As noted above, in some embodiments, the medical image database 110 is combined with the server 105. Alternatively or in addition, the medical images 165 may be stored within a plurality of databases, such as within a cloud service. Although not illustrated in FIG. 1, the medical image database 110 may include components similar to the server 105, such as an electronic processor, at least one memory, a communication interface, and the like. For example, the medical image database 110 may include a communication interface configured to communicate (for example, receive data and transmit data) over the communication network 120.

In some embodiments, the medical image database 110 stores additional data associated with the medical images 165, such as a classification associated with each of the medical images 165. In other embodiments, this information (along with the associated image data) may be stored separate from the medical image database 110. The medical image database 110 may also store acquired or captured medical images that are not part of a training dataset.

The learning engine 145 applies machine learning (artificial intelligence) to mimic cognitive functions, including but not limited to learning and problem solving. Machine learning generally refers to the ability of a computer program to learn without being explicitly programmed. In some embodiments, a computer program (sometimes referred to as a learning engine) is configured to construct a model (for example, one or more algorithms) based on example inputs. Supervised learning involves presenting a computer program with example inputs and their desired (actual) outputs. In one embodiment, the computer program is configured to learn a general rule (a contour refinement model) that maps the inputs to the outputs in the training data.

Machine learning may be performed using various types of methods and mechanisms. Example methods and mechanisms include decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using some or all of these approaches, a computer program may ingest, parse, and understand data and progressively refine models for data analytics, including image analytics. Once trained, the computer system may be referred to as an intelligent system, an artificial intelligence (AI) system, a cognitive system, or the like. Accordingly, in some embodiments, the learning engine 145 includes Watson™ provided by IBM Corporation. The learning engine 145 may be "trained" using various machine learning techniques. The learning engine 145 and contour refinement model 150 are operated to improve contours of lesions provided in images as follows.

Single Phase Contour Refinement

Figure 2:
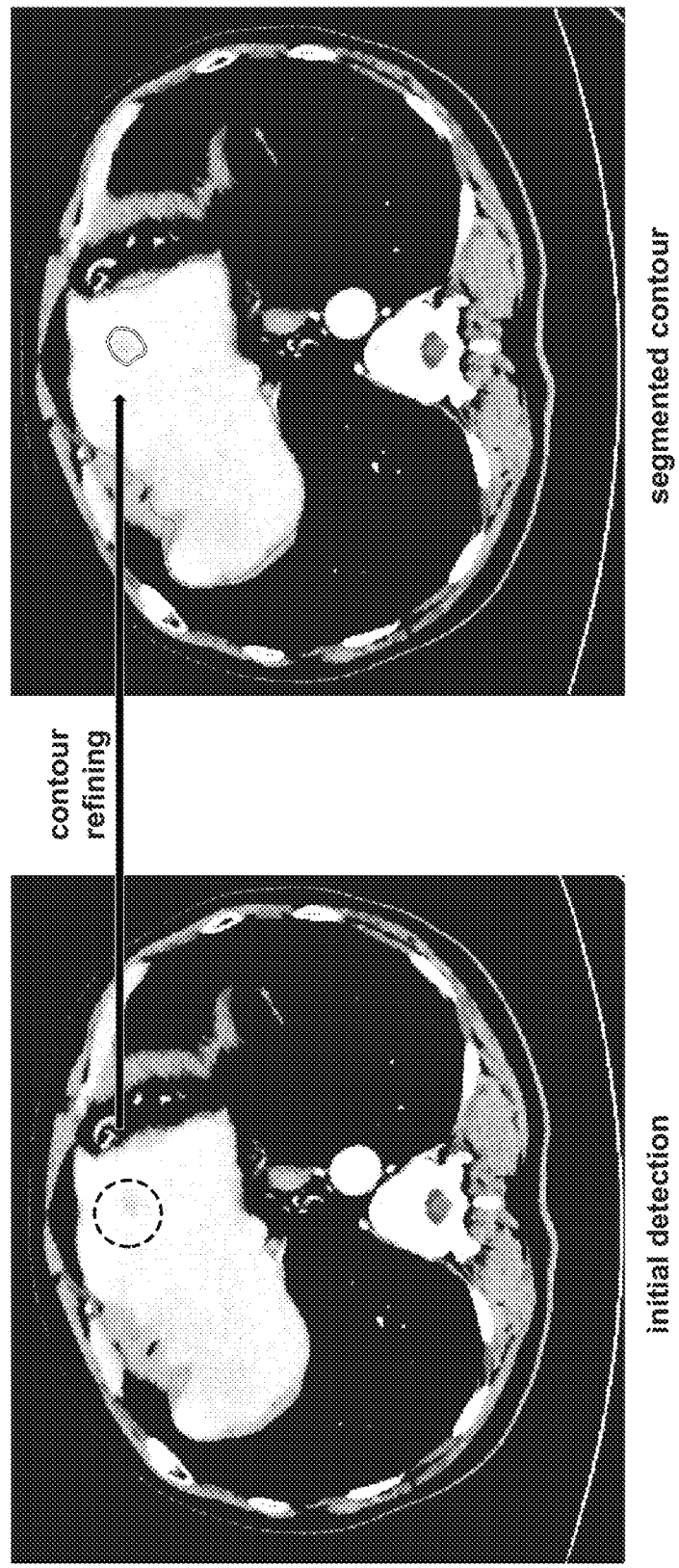
FIG. 2 shows an image for an initial detection of a lesion and an image of a segmented contour of the lesion after contour refinement.

FIG. 2 shows a detection of a lesion located within a circle 180 for purposes of illustration. After detection of the lesion, contour refinement occurs as shown in the flowchart 200 of FIG. 3.

Figure 3:
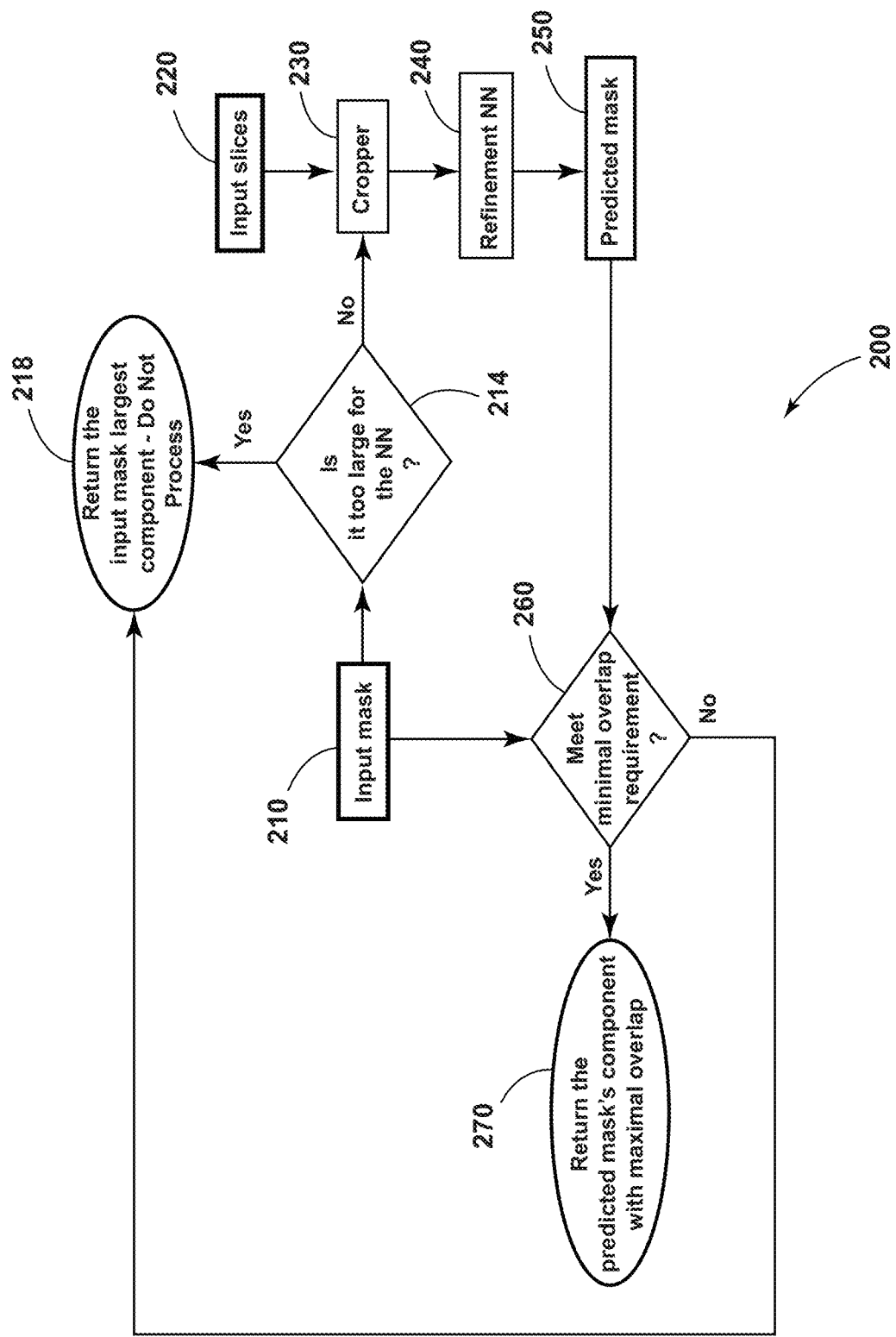
FIG. 3 illustrates a flowchart for one embodiment of contour refinement.

FIG. 3 is a flowchart illustrating an a method 00 performed by the server 105 (i.e., the electronic processor 125 executing a set of instructions, such as the contour refinement model 150) for automatically selecting, arranging, and processing medical images according to some embodiments. As noted above, in some embodiments, the user device 115 may be configured to execute one or more software applications to perform all or a portion of the functionality described herein as being performed via execution of the contour refinement model 150.

In FIG. 3, the electronic processor 125 is configured to provide a three dimensional (3D) input mask (at step 210). The 3D input mask is a stored predetermined region. The electronic processor 125 advances to decision step 214. At decision step 214, the electronic processor 125 determines whether the 3D input mask 210 is too large for the neural network that processes images. If the 3D input mask is too large, the electronic processor 125 advances to step 218. At step 218, due to the 3D input mask having a largest component, the 3D input mask is not processed and is returned. A different input mask is required to attempt to execute the contour refinement model 150 set forth in the flowchart 200.

Meanwhile, at step 220, input slices of computer images, such as a computed tomography (CT) scan or a positron emission tomography (PET) scan are provided to the contour refinement model 150. In one embodiment, 16 input slices are provided. When the 3D input mask is not too large for the neural network, the electronic processor 125 advances to cropper step 230. At cropper step 230, the electronic processor 125 extracts sub-images whose dimension typically exceeds that of the 3D mask, itself a 3D object, so that the mask fits. Thus, the electronic processor 125 crops the input slices to remove a sub-portion of the input slices. The sub-images are then provided for analysis by the contour refinement model 150. Areas or another sub-portion outside of the sub-images are not analyzed by the contour refinement model 150. Cropping of the input image slices reduces the amount of analysis required for a lesion. A neural network or the electronic processor 125 operates on the cropped input slices and the 3D input mask.

FIG. 4A shows an un-augmented training example wherein the input mask having an input contour I surrounds a portion of a target contour T. The input contour I corresponds to the input mask 210 provided thereto. Two random examples of augmented data sensing are provided in FIG. 4B where in the input contour I is always disposed at the center of the image in two augmented training examples. In the two data augmentation examples illustrated in FIG. 4C, variable input contour I and target contour T positions are provided. FIGS. 4A-4C are virtual images for purposes of discussion, not actual lesions.

Returning to FIG. 3, the single phase contour refinement occurs at step 240 by the electronic processor 125 communicating with a neural network to determine a contour and boundary for a detected lesion. Utilizing the contour refinement model 150, a three dimensional (3D) predicted mask 250 is presented. The predicted 3D mask 250 corresponds to a likely position for the target contour T.

Thereafter, the electronic processor 125 advances to decision step 260 and determines whether the minimal overlap requirement is met with respect to the 3D input mask and the 3D predicted mask. If not, the decision step 260 advances to step 218 and the 3D predicted mask is not utilized and is reverted to the 3D input mask. Thus, the 3D predicted mask is stored only when the 3D predicted mask meets the minimal overlap requirements. If the overlap requirements are not met, the 3D input mask can be provided as the output mask. The minimum requirement at step 260 can be set to zero in some embodiments. Thus, the minimum requirement is an optional feature.

If the electronic processor 125 determines that the 3D predicted mask meets the minimal overlap requirement, the electronic processor 125 advances to step 270. At step 270, the 3D predicted mask is utilized for determining the contour of a lesion. Storing of the 3D predicted mask includes a 3D lesion contour for single phase medical images.

Figure 5:
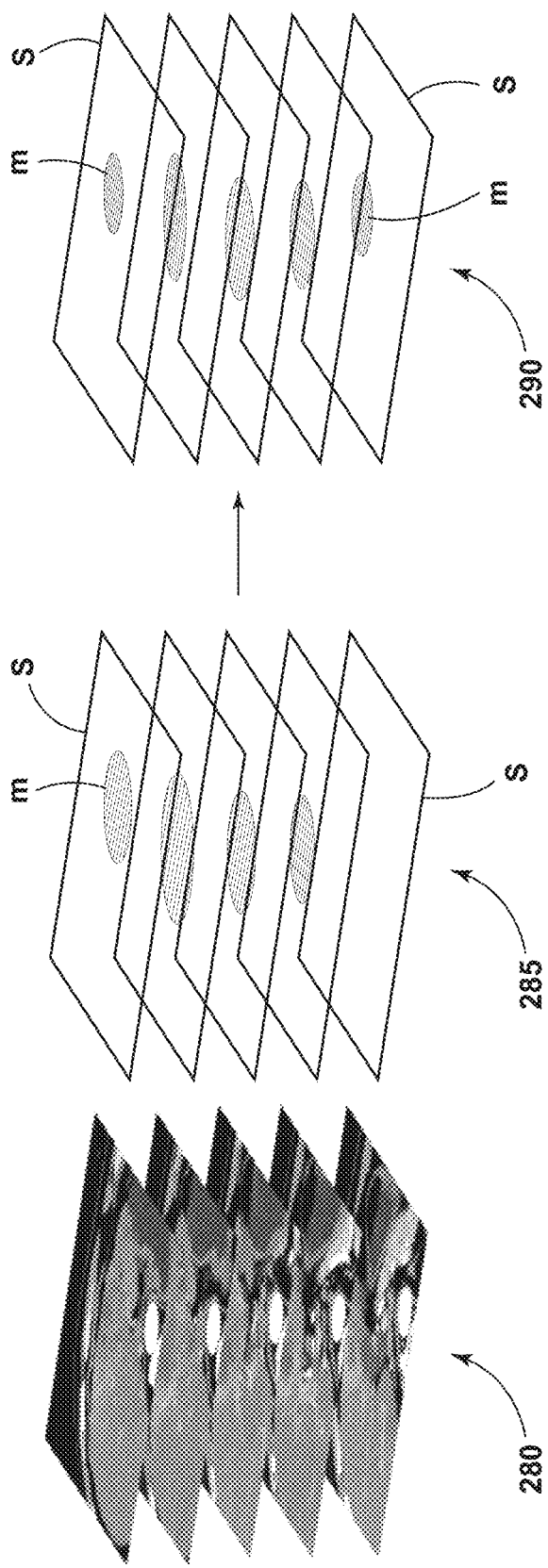
FIG. 5 shows image slices, an input mask, and a contour refined mask for one embodiment.

FIG. 5 shows five image slices 280 of an organ including a lesion. FIG. 5 also shows a 3D mask 285 that is obtained for the lesion without contour refinement. Note that the 3D mask 285 includes mask slices S having a region of interest M, but the bottom slice of the mask slices S does not include a region of interest M thereon without contour refinement. Upon execution of contour refinement by an electronic processor 125 or other processing arrangements, the bottom one of the mask slices S of the corresponding refined mask 290 includes a region of interest M. The regions of interest M, in combination, define the 3D refined mask 290. The 3D refined mask 290 provided with the refined mask slices S provides an outline for a three dimensional (3D) lesion in single phase medical images. While five image slices 280 and five mask slices S are shown in FIG. 5, sixteen slices or any other plurality of slices are contemplated.

In one embodiment, the contour refinement model 150 may be initially created or modified using machine learning. Machine learning generally refers to the ability of a computer program to learn without being explicitly programmed. In some embodiments, a computer program (e.g., a learning engine) is configured to construct a model (e.g., one or more algorithms) based on example inputs. Supervised learning involves presenting a computer program with example inputs and their desired (e.g., actual) outputs. The computer program is configured to learn a general rule (e.g., a model) that maps the inputs to the outputs. The computer program may be configured to perform deep machine learning using various types of methods and mechanisms. For example, the computer program may perform deep machine learning using decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics.

Figure 6:
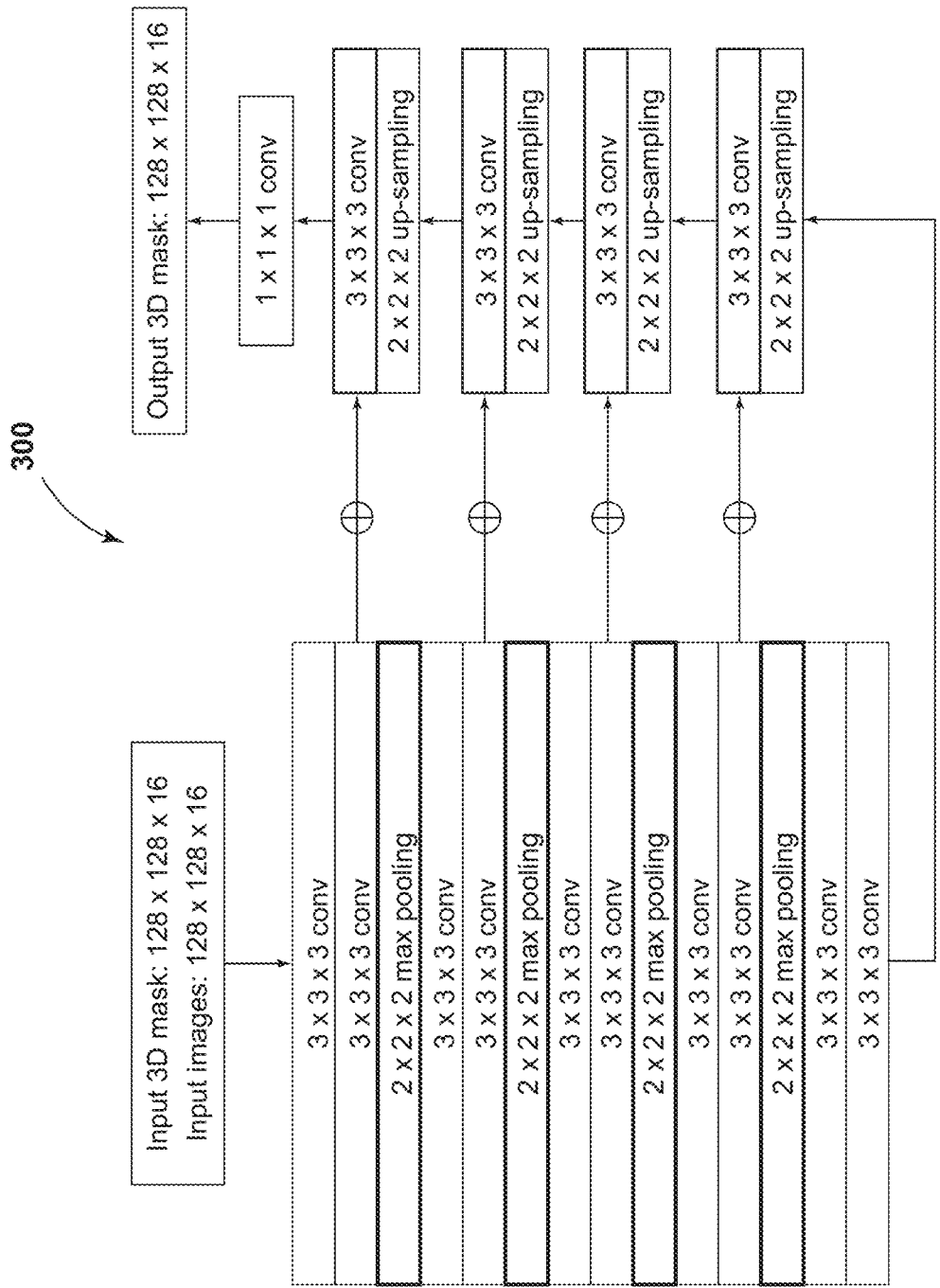
FIG. 6 shows an architecture for one embodiment of contour refinement.

In one embodiment, the contour refinement model 150 is performed by a U-Net 3D model that enables deep learning. FIG. 6 shows architecture 300 for a 3D U-Net that is provided with a 3D input mask and input images or slices having a resolution of 128×128×16. The architecture 300 processes the input mask and input images to generate a 3D predicted or output mask for a lesion. In one embodiment, the Chan-Vese algorithm is utilized. Other algorithms to perform contour refinement are also contemplated.

In some instances, several 3D lesions could be present in proximity to each other. The algorithm could show serious side effects that might merge the cross sections of different lesions into one single all-encompassing contour, which would destroy 3D lesion identities. To prevent such an occurrence, lesion contour refinement is performed on one lesion at a time.

While an electronic processor 125 is mentioned above as executing the steps shown in FIG. 3, a neural network that is a set of mathematical operations can be performed partly or entirely on one or more servers 105 or other computing devices. In another embodiment, the neural network is provided on a single computing device. In another embodiment, the electronic processor 125 is a node implementing operation of the neural network.

Multiphase Contour Refinement

Figure 7:
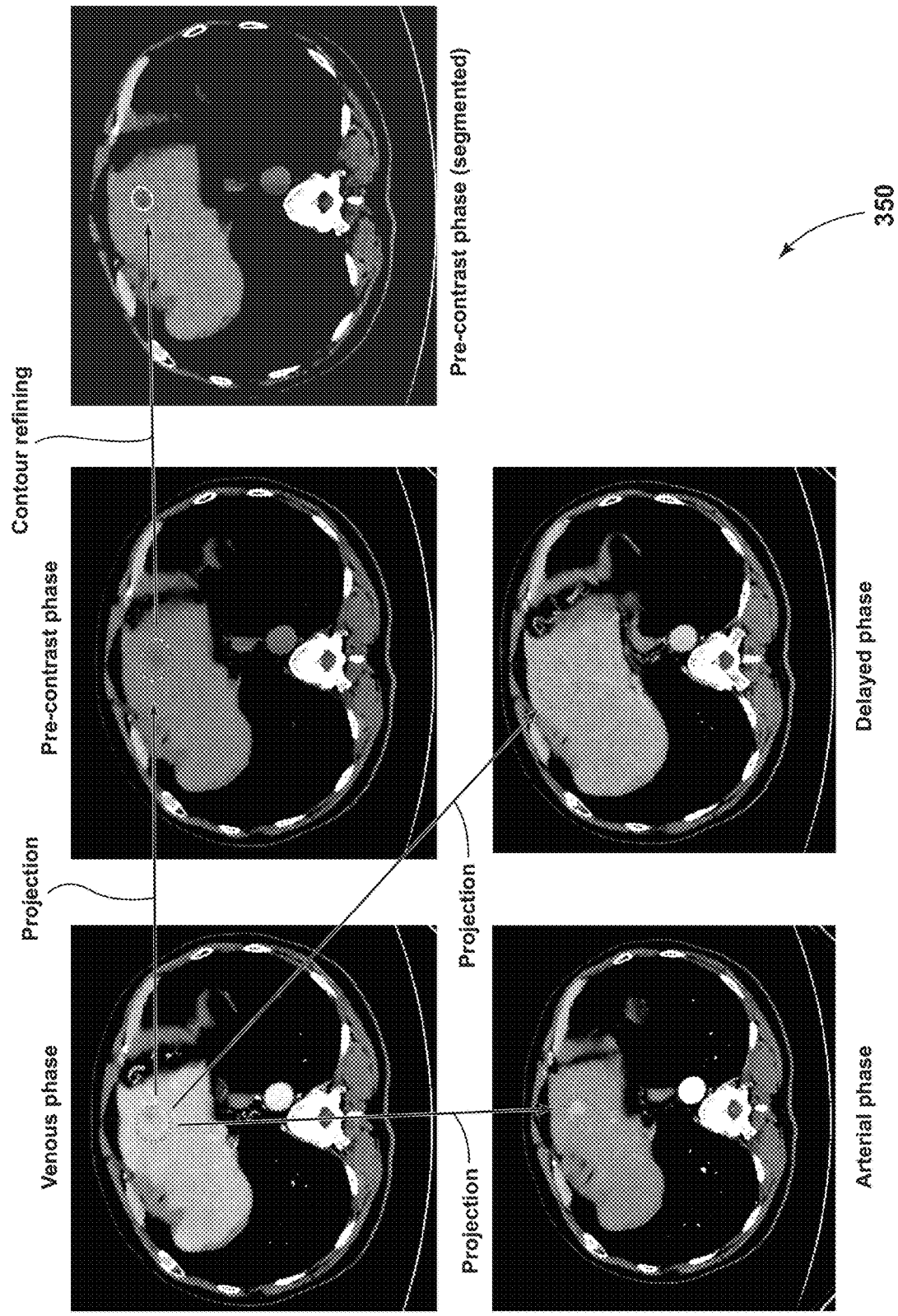
FIG. 7 shows a plurality of images of the same organ, and includes a contour refined image.

FIG. 7 shows a collection 350 of medical images of an organ that includes a lesion. The CT medical images include a venous phase, an arterial phase, a pre-contrast phase, and a delayed phase for the same organ. Further, a contour refined pre-contrast phase image is also illustrated. The medical images are taken at different phases (time). Thus, a small amount of movement of the organ viewed in the different phases may be realized and must be accounted for. To obtain contour refinement of images in the additional phases, the 3D lesion contour already obtained in the reference phase or single phase is utilized.

In one embodiment, the reference phase is the venous phase, which has already been segmented as set forth in FIGS. 1-5 to obtain in a 3D contour of a lesion in the venous phase. The 3D contour may be considered as a binary 3D mask for the reference phase, which in this example is the venous phase. There are two methods for performing multiphase lesion contour refinement.

Deformation of the Reference Mask to the New Phase

In a first multiphase embodiment, the lesion contour refinement is performed in a new phase or target phase. A target phase describes a new phase different from the reference phase. In one embodiment, the reference phase medical images are from the venous phase. Thus, the target phase medical images are from a group consisting of the arterial phase, the pre-contrast phase, and the delayed phase to be displayed in this instance.

FIG. 8 shows a flowchart 400, wherein a binary 3D mask 410 corresponding to the venous phase is provided for use in the lesion contour refinement of a lesion in an arterial phase in one embodiment. The binary 3D mask or refinement contour for the venous phase previously determined as the 3D predicted mask 250 in FIG. 3 is provided to a venous to arterial deformation field in the first multiphase embodiment. A target-reference deformation field 420 is contemplated wherein the reference phase is the phase from which the previously determined predicted mask originated and the target phase is a different phase. Thus, the target reference deformation field 420 deforms the binary 3D mask for the reference phase coordinate system to provide a deformed input mask 430 for the target phase coordinate system.

In one embodiment, the venous to arterial deformation field 420 is computed by the electronic processor 125 based on the arterial and venous images, and identifies for an arbitrary pixel site in the venous image, its corresponding pixel site in the arterial image, such that both sites represent the same biological point positions inside a patient's abdomen under different viewing conditions and times. Thus, the binary 3D mask of the venous phase for a lesion is relocated to form a deformed input mask for the arterial phase image in the arterial phase coordinate system. Deforming the 3D input mask to correspond to point positions for a target phase coordinate system of the medical images obtains a deformed 3D input mask corresponding to the target phase.

Thereafter, the lesion contour refinement is executed on the arterial phase images by executing the lesion contour refinement process illustrated in FIG. 3 as previously discussed. Thus, lesion contour refinement of the arterial phase images using the deformed input mask operates with ease and obtains a 3D lesion contour or 3D predicted mask for display in the arterial phase coordinate system for an organ in one embodiment.

The deformation field 420 may be considered a target-reference deformation field in every embodiment. The target phase is the arterial phase and the reference phase is a venous phase for the target-reference deformation field in the embodiment described above. Other arrangements are contemplated for the target-reference deformation field, such as wherein the reference phase is the arterial phase and the target phase is one of from a group consisting of the venous phase, the pre-contrast phase, the delayed phase, and the like.

Warping of the New Phase Images to the Reference Phase

Figure 10A:
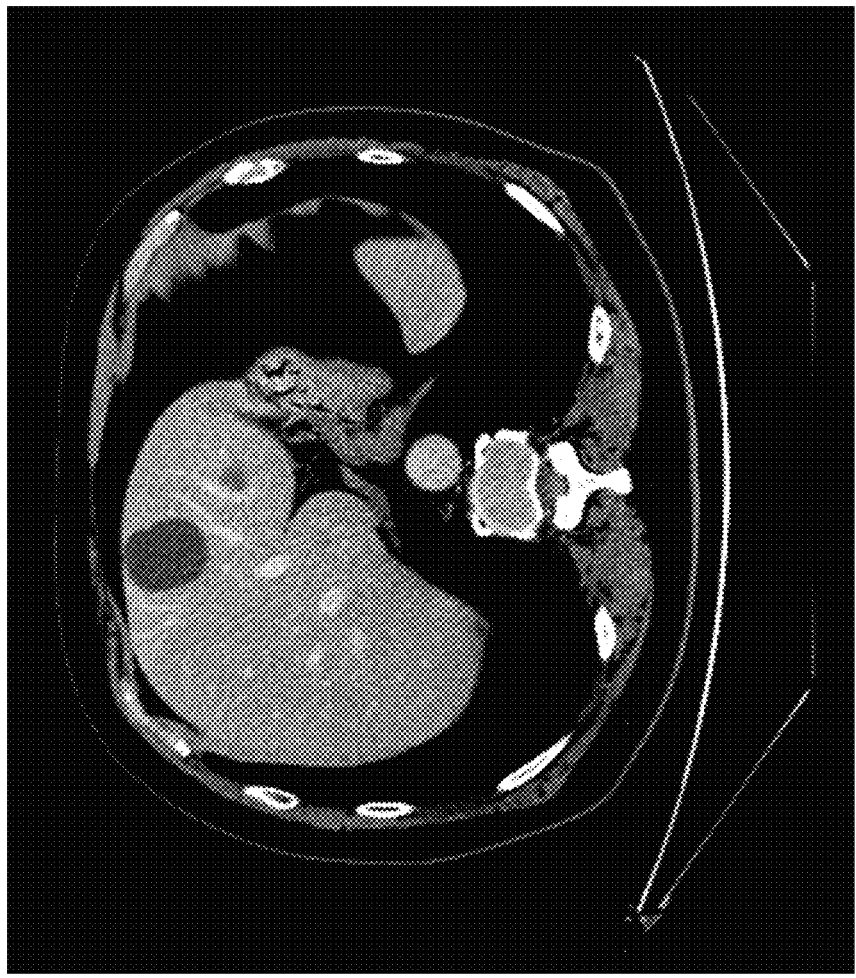
FIG. 10A shows a venous phase slice and FIG. 10B shows the corresponding registered arterial phase slice.
Figure 10B:
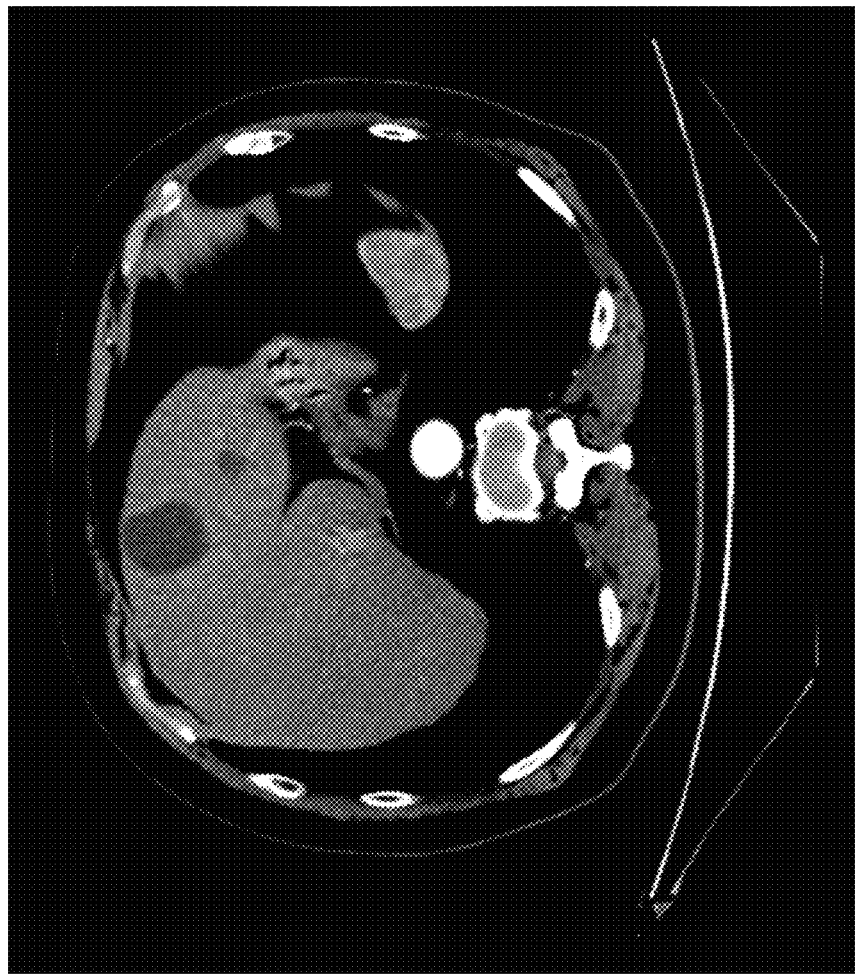

In another embodiment shown in the flowchart 500 of FIG. 9, a different approach is taken to obtain lesion contour refinement of the target phase images. In this instance, input image slices of the arterial phase images or another target phase 510 are provided to a target-reference deformation field 520. The target reference deformation field 520 deforms image slices 510 from the target phase coordinate system to warped input slices 530 for the reference phase coordinate system. In one embodiment, the target-reference deformation field 520 operates to register arterial images at each pixel site in the venous image slices, by setting a value corresponding to the pixel site of the venous phase image to the intensity copied from an arterial phase pixel site identified by the arterial-venous deformation field. The deformation field or warping step 520 outputs warped input slices 530 from the arterial image slices that are now registered or in alignment with the venous coordinate system. FIG. 10A shows a venous phase image for purposes of reference. FIG. 10B shows an arterial phase image that is warped or registered to the venous phase coordinate system. Thus, the images are corresponding to the same slice in the venous phase coordinate system as displayed. Deforming the input image slices causes the slices to correspond to the point position of the reference phase coordinate system, which is the venous phase coordinate system in this embodiment, as warped input slices.

Thereafter, the lesion contour refinement shown in FIG. 3 is operated upon the arterial image slices that are warped to correspond to the venous image slices in terms of position in the venous coordinate system. The FIG. 3 operation includes the 3D binary contour that was determined during the venous phase as the input binary 3D mask. As the warped images correspond to the venous phase coordinate system, a 3D predicted mask having a 3D contour result is obtained in FIG. 3 for the arterial phase that, however, relates to the venous phase coordinate system.

Figure 11:
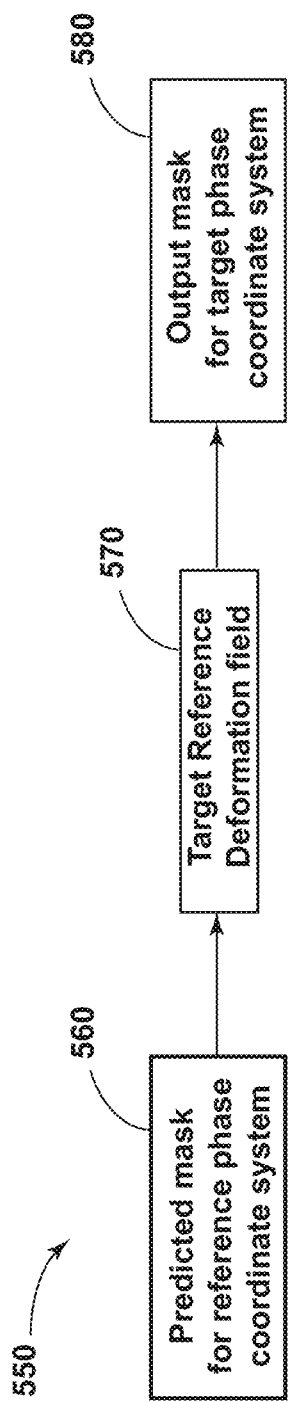
FIG. 11 shows a flowchart for deforming a predicted mask to correspond to a target phase coordinate system.

In order to display the 3D contour obtained for warped arterial phase images, the calculated 3D contour or 3D predicted mask must be returned to the arterial phase coordinate system. FIG. 11 shows a flowchart 550 that operates to do so. A predicted mask for the reference phase coordinate system is provided to a target reference deformation field 570. The deformation field 570 deforms the 3D predicted mask resulting in an output mask 580 for the target phase coordinate system for display. In the embodiment wherein the predicted 3D mask 560 is in a venous phase coordinate system, the 3D mask is provided to a venous-arterial deformation field 570. The venous-arterial deformation field 570 operates to map the 3D predicted mask 560 in the venous coordinate system to the arterial coordinate system as a 3D output mask 580. Thus, the 3D predicted mask is mapped to the arterial phase images as the 3D output mask. The 3D output mask 580 is a 3D contour of arterial phase medical images for display of a lesion.

While a venous-arterial deformation field is discussed herein, the target reference deformation field 420, 520, 570 is used to represent any of the pre-contrast phase, arterial phase, and delayed phase being utilized as the reference phase instead of the venous phase. Further, the pre-contrast phase or delayed phase can be used as the target phase to be provided with contour refinement, instead of the arterial phase. FIG. 7 shows the pre-contrast phase as being provided with contour refining, for example. Such contour refining would include a pre-contrast-venous deformation field in another embodiment.

Figure 12A:
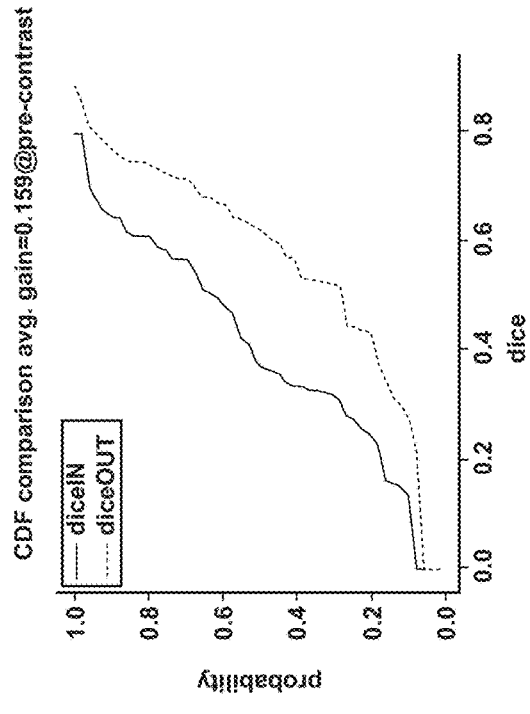
FIGS. 12A-12D show graphs of contour refinement results for various phases.
Figure 12C:
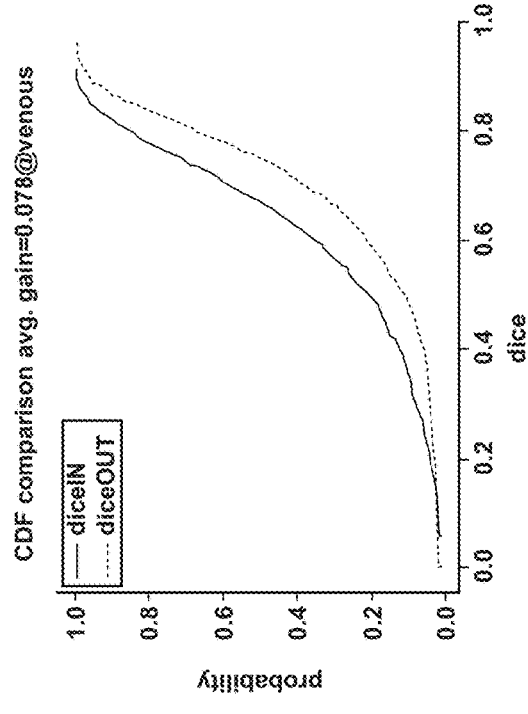
Figure 12B:
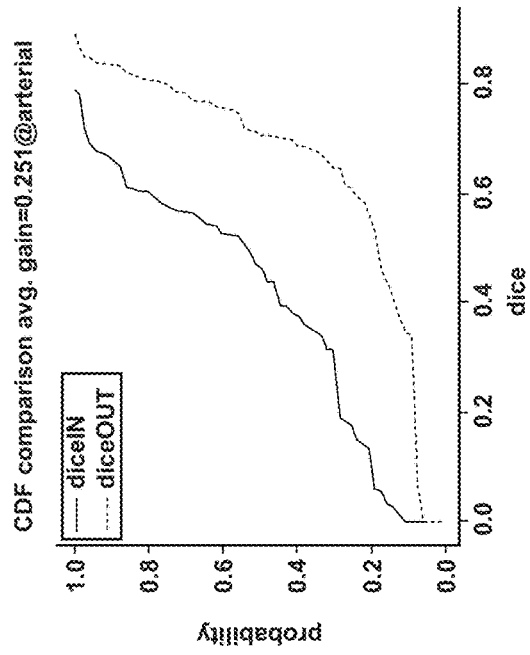
Figure 12D:
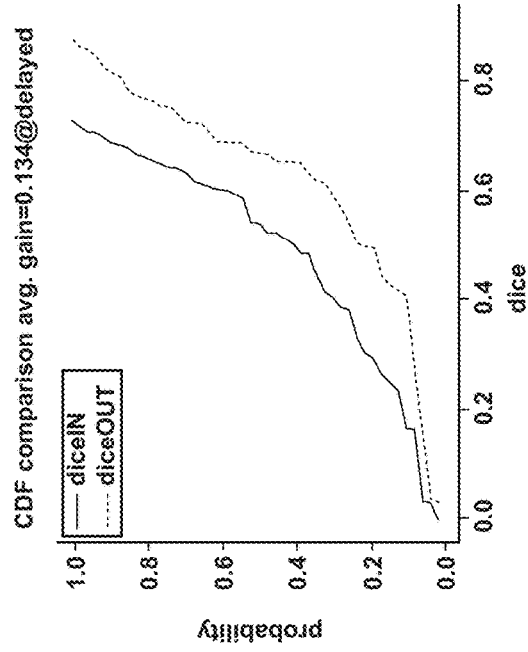

FIGS. 12A-12D show the improvement provided by the multiphase contour refinement for the instance segmentation of lesions in the multiphase medical images. For instance, FIG. 12A shows a cumulative distribution function (CDF) of the dice coefficients of the lesion contours before and after contour refinement for the contour refinement in the arterial phase. The leftward oriented CDF curve is from before contour refinement and the rightward oriented CDF curve is from after contour refinement. FIG. 12B shows improvement in the CDF curve in the delayed phase. FIG. 12C shows improvement for the CDF curve in the pre-contrast phase after contour refinement and FIG. 12D shows improvement for the CDF curve after contour refinement in the venous phase. These are examples of the advantage gained from performing lesion contour refinement of multiphase medical images.

Thus, embodiments described herein provide, among other things, methods and systems for providing contour refinement of a detected lesion in medical images. Machine learning techniques may be used to establish or modify such a contour refinement model 150, which further improve the efficiency and effectiveness of the systems and methods. Various features and advantages of the invention are set forth in the following claims.

What is claimed is:

1. A system for providing lesion contour refinement for multiphase medical images of an organ, the system comprising:
   a display device;
   at least one memory for storing medical images; and
   an electronic processor configured to:
      receive a 3D input mask corresponding to a lesion contour determined for a reference phase of the multiphase medical images;
      deform the 3D input mask to correspond to point positions for a target phase coordinate system of the medical images to obtain a deformed input mask corresponding to a target phase;
      receive input slices from the target phase medical images that includes a lesion;
      crop the input slices to remove a sub-portion of the input slices;
      perform lesion contour refinement for the cropped input slices and the 3D input mask to obtain a 3D predicted mask;
      determine whether the 3D predicted mask meets a minimal overlap requirement, and only storing the 3D predicted mask when the 3D predicted mask meets the minimal overlap requirement; and
      store the 3D predicted mask for the target phase to provide a 3D lesion contour.

2. The system of claim 1, wherein the electronic processor is configured to, when the 3D predicted mask does not meet the minimal overlap requirement, provide the 3D input mask as a 3D output mask.

3. The system of claim 1, wherein the reference phase is the venous phase and the target phase is one from a group consisting of the delayed phase, the arterial phase, and the pre-contrast phase, and wherein the lesion contour refinement is performed by a neural network.

4. The system of claim 3, wherein the electronic processor is configured to determine whether the 3D input mask is too large for the neural network, and wherein the 3D input mask is not processed when the 3D input mask is too large for the neural network.

5. The system of claim 1, wherein the input slices are from computer tomography images that include a lesion.

6. The system of claim 1, wherein the lesion contour refinement is performed by a neural network that is executed by the electronic processor.

7. The system of claim 1, wherein the electronic processor is configured to determine whether the 3D input mask is too large, wherein the 3D input mask is not processed when the 3D input mask is too large.

8. A method for providing lesion contour refinement for multiphase medical images of an organ, the method comprising:
   receiving a 3D input mask corresponding to a lesion contour determined for a reference phase of the multiphase medical images;
   deforming the 3D input mask to correspond to point positions for a target phase coordinate system of the medical images to obtain a deformed input mask corresponding to a target phase;
   providing the deformed 3D input mask to a neural network;
   receiving input slices from the target phase medical images that includes a lesion;
   cropping the input slices to remove a sub-portion of the input slices;
   performing lesion contour refinement for the cropped input slices and the 3D input mask to obtain a 3D predicted mask;
   determining whether the 3D predicted mask meets a minimal overlap requirement, and only storing the 3D predicted mask when the 3D predicted mask meets the minimal overlap requirement; and
   storing the 3D predicted mask for the target phase to provide a 3D lesion contour.

9. The method of claim 8, including when the 3D predicted mask does not meet the minimal overlap requirements, providing the 3D input mask as the 3D output mask.

10. The method of claim 8, including determining whether the 3D input mask is too large for the neural network, and wherein the 3D input mask is not processed when the 3D input mask is too large for the neural network.

11. The method of claim 8, wherein the reference phase is the venous phase and the target phase is one from a group consisting of the delayed phase, the arterial phase, and the pre-contrast phase, and wherein the lesion contour refinement is performed by a neural network.

12. The method of claim 11, including determining whether the 3D input mask is too large for the neural network, and wherein the 3D input mask is not processed when the 3D input mask is too large for the neural network.

13. A non-transitory computer medium including instructions that, when executed as a set of instructions by an electronic processor perform a set of operations comprising:
   receiving a 3D input mask corresponding to a lesion contour determined for a reference phase of multiphase medical images;
   deforming the 3D input mask to correspond to point positions for a target phase coordinate system of the medical images to obtain a deformed input mask corresponding to a target phase;
   receiving input slices from the target phase medical images that includes a lesion;
   cropping the input slices to remove a sub-portion of the input slices;
   performing lesion contour refinement for the cropped input slices and the 3D input mask to obtain a 3D predicted mask;
   determining whether the 3D predicted mask meets a minimal overlap requirement, and only storing the 3D predicted mask when the 3D predicted mask meets the minimal overlap requirement; and
   storing the 3D predicted mask for the target phase to provide a 3D lesion contour.

14. The non-transitory computer medium of claim 13, wherein the input slices are from computer tomography images that include a lesion.

15. The non-transitory computer medium of claim 13, wherein the lesion contour refinement is performed by a neural network that is executed by the electronic processor.

16. The non-transitory computer medium of claim 15, wherein the instructions executed by the electronic processor determine whether the 3D input mask is too large for the neural network, and the 3D input mask is not processed when the 3D input mask is too large for the neural network.

17. The non-transitory computer medium of claim 16, wherein the instructions executed by the electronic processor determine whether the 3D predicted mask meets a minimal overlap requirement; and only store the 3D predicted mask when the 3D predicted mask meets the minimal overlap requirement.

* * * * *